United States Patent
Parthasaradhi Reddy et al.

(10) Patent No.: US 9,139,535 B2
(45) Date of Patent: Sep. 22, 2015

(54) PROCESS FOR RILPIVIRINE USING NOVEL INTERMEDIATE

(71) Applicants: Bandi Parthasaradhi Reddy, Hyderabad (IN); Kura Rathnakar Reddy, Hyderabad (IN); Dasari Muralidhara Reddy, Hyderabad (IN); Adulla Venkat Narsimha Reddy, Hyderabad (IN); Bandi Vamsi Krishna, Hyderabad (IN)

(72) Inventors: Bandi Parthasaradhi Reddy, Hyderabad (IN); Kura Rathnakar Reddy, Hyderabad (IN); Dasari Muralidhara Reddy, Hyderabad (IN); Adulla Venkat Narsimha Reddy, Hyderabad (IN); Bandi Vamsi Krishna, Hyderabad (IN)

(73) Assignee: Hetero Research Foundation (IN)

( * ) Notice: Subject to any disclaimer, the term of this patent is extended or adjusted under 35 U.S.C. 154(b) by 0 days.

(21) Appl. No.: 14/589,622

(22) PCT Filed: Jul. 8, 2013

(86) PCT No.: PCT/IN2013/000415
§ 371 (c)(1),
(2) Date: Jan. 5, 2015

(87) PCT Pub. No.: WO2014/009968
PCT Pub. Date: Jan. 16, 2014

(65) Prior Publication Data
US 2015/0183751 A1    Jul. 2, 2015

(30) Foreign Application Priority Data
Jul. 12, 2012 (IN) .......................... 2832/CHE/2012

(51) Int. Cl.
*C07D 239/42* (2006.01)
*C07D 239/48* (2006.01)

(52) U.S. Cl.
CPC ............ *C07D 239/48* (2013.01); *C07D 239/42* (2013.01)

(58) Field of Classification Search
CPC ........................... C07D 239/42; C07D 239/48
See application file for complete search history.

(56) References Cited

U.S. PATENT DOCUMENTS

| | | | |
|---|---|---|---|
| 7,125,879 B2 * | 10/2006 | Guillemont et al. | .......... 514/256 |
| 7,241,458 B1 | 7/2007 | Verreck et al. | |
| 7,705,148 B2 | 4/2010 | Schils et al. | |
| 8,153,640 B2 | 4/2012 | Guillemont et al. | |

FOREIGN PATENT DOCUMENTS

| WO | 2014009968 A2 | 1/2014 |
| WO | 2014009968 A3 | 1/2014 |

OTHER PUBLICATIONS

International Written Opinion of PCT/IN2013/000415 dated Jan. 22, 2014.
International Search Report of PCT/IN2013/000415 dated Jan. 22, 2014.

* cited by examiner

*Primary Examiner* — Erich A Leeser
(74) *Attorney, Agent, or Firm* — Caesar Rivise, PC

(57) ABSTRACT

The present invention provides a commercially viable process for preparing rilpivirine and its pharmaceutically acceptable acid addition salts thereof in high yields using novel intermediate.

10 Claims, No Drawings

PROCESS FOR RILPIVIRINE USING NOVEL INTERMEDIATE

This application is a national stage application of PCT/IN2013/000415 filed Jul. 8, 2013 which claims the benefit of Indian patent Application No. 2832/CHE/2012, filed on Jul. 12, 2012, which is incorporated herein by reference.

FILED OF THE INVENTION

The present invention provides a commercially viable process for preparing rilpivirine and its pharmaceutically acceptable acid addition salts thereof in high yields using novel intermediate.

BACKGROUND OF THE INVENTION

Rilpivirine hydrochloride, chemically 4-[[4-[[4-(2-cyanoethenyl)-2,6-dimethylphenyl]amino]pyrimidinyl]amino]benzonitrile hydrochloride and has the structural formula:

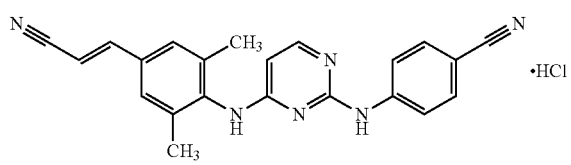 [SMILES: Cc1cc(/C=C/C#N)cc(C)c1Nc1ccnc(Nc2ccc(C#N)cc2)n1 ; Cl]

Rilpivirine (TMC278) is an investigational new drug, developed by Tibotec, for the treatment of HIV infection. It is a second-generation non-nucleoside reverse transcriptase inhibitor (NNRTI) with higher potency, longer half-life and reduced side-effect profile compared with older NNRTIs.

Rilpivirine and its hydrochloride salt were disclosed in U.S. Pat. No. 7,125,879.

Process for the preparation of rilpivirine was disclosed in U.S. Pat. No. 7,399,856 ('856 patent). According to the '856 patent, rilpivirine can be prepared by reacting the (E)-3-(4-amino-3,5-dimethylphenyl)acrylonitrile hydrochloride of formula II with 4-(4-chloropyrimidin-2-ylamino)benzonitrile of formula III-a in the presence of potassium carbonate and acetonitrile under reflux for 69 hours. The synthetic procedure is illustrated in scheme I, below:

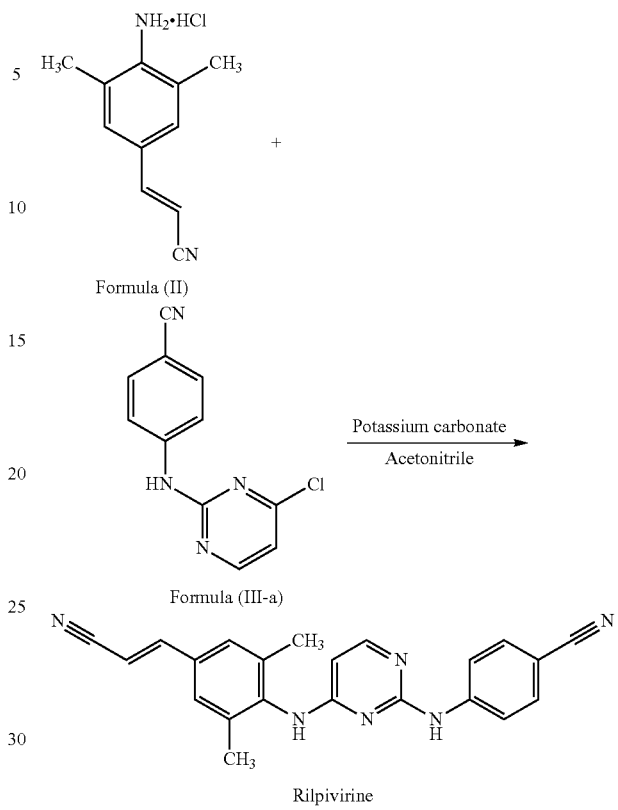

According to the '856 patent, 4-(4-chloropyrimidin-2-ylamino)benzonitrile of formula III-a can be prepared by reacting the 4-[(1,4-dihydro-4-oxo-2-pyrimidinyl)amino]benzonitrile with phosphorus oxytrichloride in the presence of methylene chloride and 2-propanone.

Process for the preparation of rilpivirine was disclosed in U.S. Pat. No. 7,705,148 ('148 patent). According to the '148 patent, rilpivirine can be prepared by reacting the 4-[[4-[[4-bromo-2,6-dimethylphenyl]amino]-2-pyrimidinyl]amino]benzonitrile with acrylonitrile in the presence of palladium acetate, N,N-diethylethanamine and tris(2-methylphenyl)phosphine in acetonitrile.

According to the '148 patent, rilpivirine can be prepared by reacting the compound of formula IV with 4-(4-chloropyrimidin-2-ylamino)benzonitrile formula III-a in the presence of hydrochloric acid and n-propanol to obtain a compound of formula VII, and then the compound was treated with acetonitrile and potassium carbonate under reflux for 69 hours. The synthetic procedure is illustrated in scheme II, below:

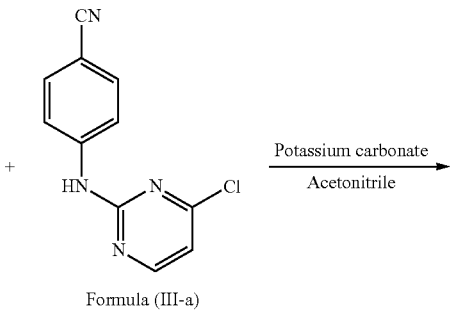

-continued

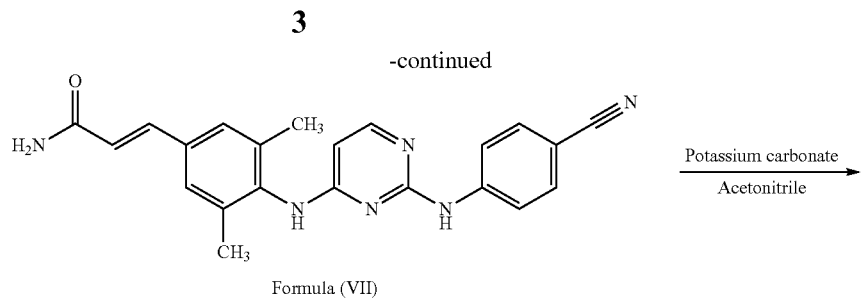

Formula (VII)

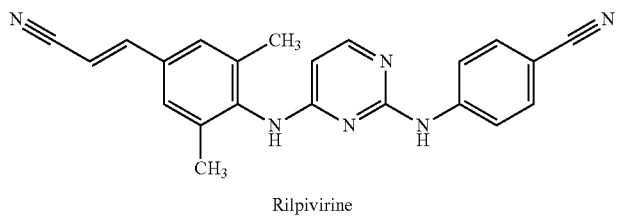

Rilpivirine

According to the '148 patent, 4-(4-chloropyrimidin-2-ylamino)benzonitrile of formula III-a can be prepared by reacting the 4-[(1,4-dihydro-4-oxo-2-pyrimidinyl)amino]benzonitrile with phosphorus oxytrichloride in the presence of methylene chloride and 2-propanone.

U.S. Pat. No. 7,563,922 disclosed a process for the preparation of (E)-3-(4-amino-3,5-dimethylphenyl)acrylonitrile hydrochloride. According to the patent, (E)-3-(4-amino-3,5-dimethylphenyl)acrylonitrile hydrochloride can be prepared by reacting the 4-iodo-2,6-dimethyl-benzenamine in N,N-dimethylacetamide with acrylonitrile in the presence of sodium acetate and toluene, and then the solid thus obtained was reacted with hydrochloric acid in 2-propanol in the presence of ethanol and diisopropyl ether.

An unpublished application, IN 1415/CHE/2011 assigned to Hetero Research Foundation discloses a process for the preparation of rilpivirine. According to the application, rilpivirine can be prepared by reacting the 4-(4-chloropyrimidin-2-ylamino)benzonitrile with (E)-3-(4-amino-3,5-dimethylphenyl)acrylonitrile hydrochloride in the presence of p-toluene sulfonic acid monohydrate and 1,4-dioxane.

It has been found that the rilpivirine produced according to the prior art procedures involves higher number of chemical steps and results in low yields. According to the present invention rilpivirine can be obtained in higher yields and in fewer number of reaction steps than the prior art processes.

We have found a novel process for the preparation of rilpivirine and its pharmaceutically acceptable acid addition salts thereof using novel intermediate.

The process of present invention is simple, inexpensive and reproducible and is well suited on an industrial scale.

Thus, an object of the present invention is to provide a novel process for preparing rilpivirine and pharmaceutically acceptable acid addition salts thereof in high yields using novel intermediate.

SUMMARY OF THE INVENTION

In one aspect, the present invention provides a novel process for the preparation of rilpivirine of formula I:

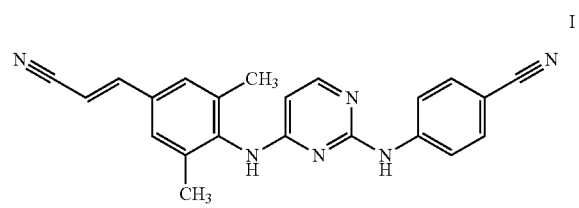 [SMILES: Cc1cc(/C=C/C#N)cc(C)c1Nc1ccnc(Nc2ccc(C#N)cc2)n1]

or a pharmaceutically acceptable salt thereof, which comprises:

a) reacting the 2,4-dichloropyrimidine of formula II:

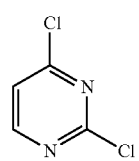

with (E)-3-(4-amino-3,5-dimethylphenyl)acrylonitrile hydrochloride of formula III:

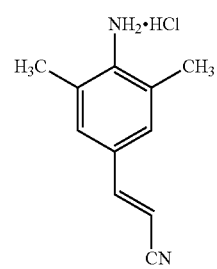

in the presence of tertiary amine and a suitable solvent to give (E)-3-(4-(2-chloropyrimidin-4-ylamino)-3,5-dimethylphenyl)acrylonitrile of formula IV; and a) reacting the 2,4-dichloropyrimidine of formula II:

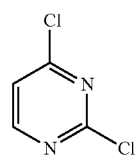

II with (E)-3-(4-amino-3,5-dimethylphenyl)acrylonitrile hydrochloride of formula III:

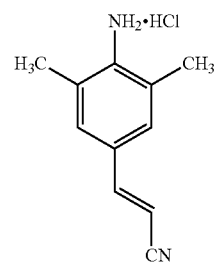

III in the presence of tertiary amine and a suitable solvent to give (E)-3-(4-(2-chloropyrimidin-4-ylamino)-3,5-dimethylphenyl)acrylonitrile of formula IV; and

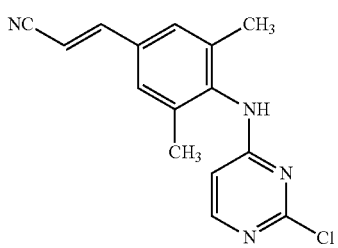

IV b) reacting the (E)-3-(4-(2-chloropyrimidin-4-ylamino)-3,5-dimethylphenyl)acrylonitrile of formula IV with 4-aminobenzonitrile of formula V in an acid and a solvent to give rilpivirine of formula I and optionally converting rilpivirine formed into the pharmaceutically acceptable acid addition salt of rilpivirine.

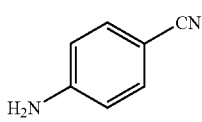

V

In another aspect, the present invention provides a novel compound of (E)-3-(4-(2-chloropyrimidin-4-ylamino)-3,5-dimethylphenyl)acrylonitrile of formula IV:

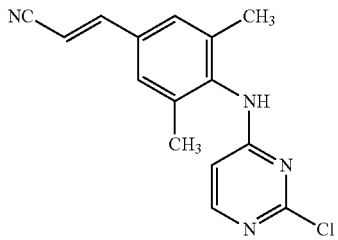

IV

DETAILED DESCRIPTION OF THE INVENTION

As used herein the term "room temperature" refers to a temperature of about 25° C. to about 35° C.

According to one aspect of the present invention, there is provided a novel process for the preparation of rilpivirine of formula I:

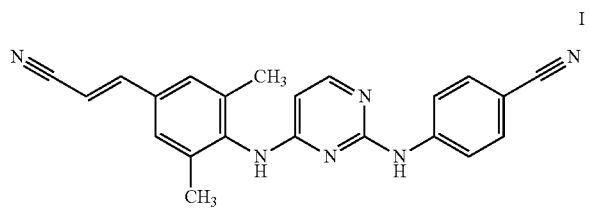 [SMILES: Cc1cc(/C=C/C#N)cc(C)c1Nc1ccnc(Nc2ccc(C#N)cc2)n1]

I or a pharmaceutically acceptable salt thereof, which comprises:

b) reacting the (E)-3-(4-(2-chloropyrimidin-4-ylamino)-3,5-dimethylphenyl)acrylonitrile of formula IV with 4-aminobenzonitrile of formula V in an acid and a solvent to give rilpivirine of formula I and optionally converting rilpivirine formed into the pharmaceutically acceptable acid addition salt of rilpivirine.

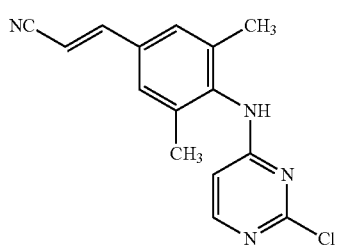

IV

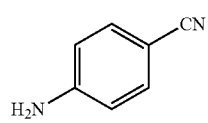

V

The suitable solvent used in step (a) may preferably be a solvent or a mixture of solvents selected from methylene chloride, ethylene dichloride, chloroform, carbon tetrachloride, ethyl acetate, methyl acetate, isopropyl acetate, tert-butyl acetate, ethyl formate and methyl formate. More preferably the suitable solvents are methylene chloride and ethyl acetate.

The tertiary amine used in step (a) may preferably be selected from N,N-diisopropylethylamine, triethylamine or trimethylamine, and more preferably the tertiary amine is N,N-diisopropylethylamine.

Preferably the solvent used in step (b) may be a solvent or a mixture of solvents selected from methanol, ethanol, isopropanol, tert-butyl alcohol, n-butanol, isobutyl alcohol, toluene, xylene, n-hexane, cyclohexane, methylene chloride, ethylene dichloride, chloroform, carbon tetrachloride, acetone, diethyl ketone, methyl ethyl ketone, methyl propyl ketone, methyl isobutyl ketone, methyl tert-butyl ketone, ethyl acetate, methyl acetate, isopropyl acetate, tert-butyl acetate, ethyl formate, methyl formate, tetrahydrofuran, diethyl ether, diisopropyl ether, tert-butyl methyl ether, dimethylformamide, N,N-dimethyl acetamide and dimethyl sulfoxide. More preferably the solvents are methanol, isopropanol, acetone, methylene chloride, diisopropyl ether and ethyl acetate.

The reaction in step (a) may preferably be carried out at ambient temperatures in the range from about 0° C. to 180° C., more preferably the step (a) is carried out at about 25° C. to 150° C.

The acid used in step (b) may preferably be selected from trifluoroacetic acid, acetic acid, p-toluenesulfonic acid or formic acid, and more preferably the acid is trifluoroacetic acid.

The reaction in step (b) may preferably be carried out at an elevated temperature. The term "elevated temperature" refers to temperature at above 25° C. More preferably the step (b) is carried out at about 40 to 90° C.

According to another aspect of the present invention, there is provided a novel compound of (E)-3-(4-(2-chloropyrimidin-4-ylamino)-3,5-dimethylphenyl)acrylonitrile of formula IV:

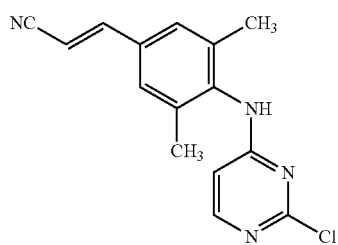

IV

The contents of rilpivirine hydrochloride and the impurities are determined by High performance liquid chromatography (HPLC).

The invention will now be further described by the following examples, which are illustrative rather than limiting.

EXAMPLES

Example 1

Preparation of (E)-3-(4-(2-chloropyrimidin-4-ylamino)-3,5-dimethylphenyl)acrylonitrile of Formula IV To a mixture of 2,4-dichloropyrimidine (25 gm) and (E)-3-(4-amino-3,5-dimethylphenyl)acrylonitrile hydrochloride (28 gm) was added N,N-diisopropylethylamine (250 ml) under stirring. The mixture was then heated to 140 to 150° C. and stirred for 55 to 60 hours. The solution was then cooled to room temperature and the solvent was distilled off under reduced pressure to provide a residual solid. To the residual solid was added ethyl acetate (1500 ml) and water (1000 ml). The reaction mass was stirred for 30 minutes at room temperature and then the layers were separated. The organic layer was dried with sodium sulfate and then concentrates to provide 30 gm of (E)-3-(4-(2-chloropyrimidin-4-ylamino)-3,5-dimethylphenyl)acrylonitrile.

Example 2

Preparation of (E)-3-(4-(2-chloropyrimidin-4-ylamino)-3,5-dimethylphenyl)acrylonitrile of Formula IV To a mixture of 2,4-dichloropyrimidine (25 gm) and (E)-3-(4-amino-3,5-dimethylphenyl)acrylonitrile hydrochloride (28 gm) was added triethylamine (300 ml) under stirring. The mixture was then heated to 140 to 150° C. and stirred for 55 to 60 hours. The solution was then cooled to room temperature and the solvent was distilled off under reduced pressure to provide a residual solid. To the residual solid was added ethyl acetate (1500 ml) and water (1000 ml). The reaction mass was stirred for 30 minutes at room temperature and then the layers were separated. The organic layer was dried with sodium sulfate and then concentrates to provide 26 gm of (E)-3-(4-(2-chloropyrimidin-4-ylamino)-3,5-dimethylphenyl)acrylonitrile.

Example 3

Preparation of (E)-3-(4-(2-chloropyrimidin-4-ylamino)-3,5-dimethylphenyl)acrylonitrile of Formula IV To a mixture of 2,4-dichloropyrimidine (5 gm) and (E)-3-(4-amino-3,5-dimethylphenyl)acrylonitrile hydrochloride (6 gm) was added N,N-diisopropylethylamine (60 ml) under stirring. The mixture was then heated to 140 to 150° C. and stirred for 55 to 60 hours. The solution was then cooled to room temperature and the solvent was distilled off under reduced pressure to provide a residual solid. To the residual solid was added methylene chloride (300 ml) and water (250 ml). The reaction mass was stirred for 30 minutes at room temperature and then the layers were separated. The organic layer was dried with sodium sulfate and then concentrates to provide 5 gm of (E)-3-(4-(2-chloropyrimidin-4-ylamino)-3,5-dimethylphenyl)acrylonitrile.

Example 4

Preparation of Rilpivirine

To a mixture of (E)-3-(4-(2-chloropyrimidin-4-ylamino)-3,5-dimethylphenyl)acrylonitrile (20 gm) as obtained in example 1,4-aminobenzonitrile (8.5 gm), isopropanol (200 ml) and trifluoroacetic acid (10 ml) were added at room temperature. The reaction mixture was then heated to 80 to 85° C. and stirred for 4 hours. The reaction mass was then cooled to 0° C. and pH was adjusted to 10 to 11 with aqueous ammonia solution. The separated solid was filtered and then dried to provide 21 gm of rilpivirine.
Chromatographic purity: 96.5%;
Content of Z-isomer: 3.0%.

Example 5

Preparation of Rilpivirine

To a mixture of (E)-3-(4-(2-chloropyrimidin-4-ylamino)-3,5-dimethylphenyl)acrylonitrile (40 gm), 4-aminobenzonitrile (17 gm), isopropanol (400 ml) and p-toluenesulfonic acid (20 ml) were added at room temperature. The reaction mixture was then heated to 80 to 85° C. and stirred for 4 hours. The reaction mass was then cooled to 0° C. and pH was adjusted to 10 to 11 with aqueous ammonia solution. The separated solid was filtered and then dried to provide 40 gm of rilpivirine.
Chromatographic purity: 96.0%;
Content of Z-isomer: 3.5%.

Example 6

Purification of Rilpivirine Hydrochloride

Rilpivirine (20 gm; Chromatographic purity: 96.5%) as obtained in example 4 was suspended in a mixture of methanol and acetone (1:1, 2000 ml) and then heated to reflux for 1 hour to provide a clear solution. The solution was treated with charcoal and filtered through celite bed. The solvent was distilled off under reduced pressure to obtain a residual solid. To the residual solid was added methanol (200 ml) and then heated to 60 to 65° C. To the solution was added a solution of hydrochloric acid in isopropanol (200 ml) at 60 to 65° C. and stirred for 1 hour 30 minutes. The contents were cooled to room temperature and stirred for 30 minutes. The separated solid was filtered and then dried to provide 15 gm of rilpivirine hydrochloride.
Chromatographic purity: 99.91%;
Content of Z-isomer: 0.07%.

Example 7

Purification of Rilpivirine Hydrochloride

Rilpivirine (20 gm; Chromatographic purity: 96.5%) was suspended in a mixture of methanol and methyl ethyl ketone (1:1, 2000 ml) and then heated to reflux for 1 hour to provide a clear solution. The solution was treated with charcoal and filtered through celite bed. The solvent was distilled off under reduced pressure to obtain a residual solid. To the residual solid was added methanol (200 ml) and then heated to 60 to 65° C. To the solution was added a solution of hydrochloric acid in isopropanol (200 ml) at 60 to 65° C. and stirred for 1 hour 30 minutes. The contents were cooled to room temperature and stirred for 30 minutes. The separated solid was filtered and then dried to provide 14 gm of rilpivirine hydrochloride.
Chromatographic purity: 99.85%;
Content of Z-isomer: 0.11%.

We claim:
1. A process for the preparation of rilpivirine of formula I:

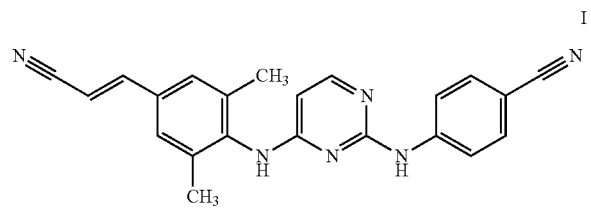 [SMILES: Cc1cc(/C=C/C#N)cc(C)c1Nc1ccnc(Nc2ccc(C#N)cc2)n1]

or a pharmaceutically acceptable salt thereof, which comprises:

a. reacting the 2,4-dichloropyrimidine of formula II:

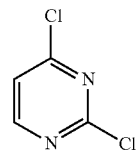

with (E)-3-(4-amino-3,5-dimethylphenyl)acrylonitrile hydrochloride of formula III:

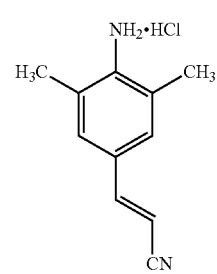

in the presence of tertiary amine and a suitable solvent to give (E)-3-(4-(2-chloropyrimidin-4-ylamino)-3,5-dimethylphenyl)acrylonitrile of formula IV; and

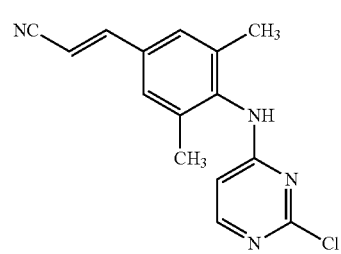

b. reacting the (E)-3-(4-(2-chloropyrimidin-4-ylamino)-3,5-dimethylphenyl)acrylonitrile of formula IV with 4-aminobenzonitrile of formula V in an acid and a solvent to give rilpivirine of formula I and optionally converting rilpivirine formed into the pharmaceutically acceptable acid addition salt of rilpivirine.

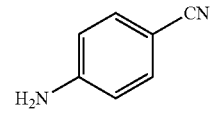

2. The process as claimed in claim 1, wherein the suitable solvent used in step (a) is a solvent or a mixture of solvents selected from methylene chloride, ethylene dichloride, chloroform, carbon tetrachloride, ethyl acetate, methyl acetate, isopropyl acetate, tert-butyl acetate, ethyl formate and methyl formate.

3. The process as claimed in claim 2, wherein the suitable solvents are methylene chloride and ethyl acetate.

4. The process as claimed in claim 1, wherein the tertiary amine used in step (a) is selected from N,N-diisopropylethylamine, triethylamine or trimethylamine.

5. The process as claimed in claim 1, wherein the reaction in step (a) is carried out at ambient temperature.

6. The process as claimed in claim 1, wherein the solvent used in step (b) is a solvent or a mixture of solvents selected from methanol, ethanol, isopropanol, tert-butyl alcohol, n-butanol, isobutyl alcohol, toluene, xylene, n-hexane, cyclohexane, methylene chloride, ethylene dichloride, chloroform, carbon tetrachloride, acetone, diethyl ketone, methyl ethyl ketone, methyl propyl ketone, methyl isobutyl ketone, methyl tert-butyl ketone, ethyl acetate, methyl acetate, isopropyl acetate, tert-butyl acetate, ethyl formate, methyl formate, tetrahydrofuran, diethyl ether, diisopropyl ether, tert-butyl methyl ether, dimethylformamide, N,N-dimethyl acetamide and dimethyl sulfoxide.

7. The process as claimed in claim 6, wherein the solvents are methanol, isopropanol, acetone, methylene dichloride, diisopropyl ether and ethyl acetate.

8. The process as claimed in claim 1, wherein the acid used in step (b) is selected from trifluoroacetic acid, acetic acid, p-toluenesulfonic acid or formic acid.

9. The process as claimed in claim 1, wherein the reaction in step (b) is carried out at an elevated temperature.

10. A novel compound of (E)-3-(4-(2-chloropyrimidin-4-ylamino)-3,5-dimethylphenyl)acrylonitrile of formula IV:

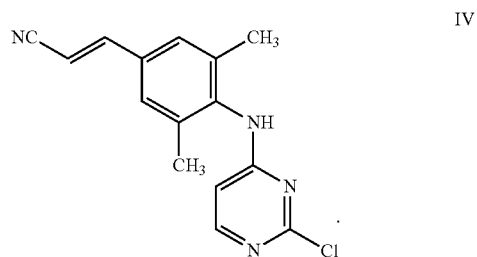 [SMILES: Cc1cc(/C=C/C#N)cc(C)c1Nc1ccnc(Cl)n1]

\* \* \* \* \*